(12) United States Patent
Pozzi (10) Patent No.: US 6,174,162 B1
(45) Date of Patent: Jan. 16, 2001

(54) INSTRUMENT FOR ADJUSTING ORTHODONTIC EXPANDER

(75) Inventor: Bruno Pozzi, Camarillo, CA (US)

(73) Assignee: American Tooth Industries, Oxnard, CA (US)

( * ) Notice: Under 35 U.S.C. 154(b), the term of this patent shall be extended for 0 days.

(21) Appl. No.: 09/469,435

(22) Filed: Dec. 27, 1999

Related U.S. Application Data (60) Provisional application No. 60/114,258, filed on Dec. 30, 1998.

(51) Int. Cl.[7] ....................................................... A61C 3/00

(52) U.S. Cl. .............................................. 433/3; 433/141

(58) Field of Search .......................................... 433/3, 141

(56) References Cited

U.S. PATENT DOCUMENTS

| 4,280,808 | * | 7/1981 | Johnsen et al. | 433/141 |
| 4,483,674 | * | 11/1984 | Schutz | 433/7 |
| 5,133,659 | * | 7/1992 | Shilliday | 433/3 |
| 5,423,677 | * | 6/1995 | Brattesani | 433/141 |
| 5,904,479 | * | 5/1999 | Staples | 433/7 |

* cited by examiner

Primary Examiner—John J. Wilson
(74) Attorney, Agent, or Firm—Emrich & Dithmar (57) ABSTRACT

An adjusting device and method of adjusting an orthodontic expander has an elongated handle and a distal extension in the form of a wire. The extension is bent at an angle of approximately 90° to form an activator tip which is inserted into the expansion screw. The handle is then rotated by one hand located entirely to one side of the medial plane of the patient's mouth, to torque the expansion screw.

12 Claims, 5 Drawing Sheets

INSTRUMENT FOR ADJUSTING ORTHODONTIC EXPANDER

CROSS REFERENCE TO RELATED APPLICATIONS

This application claims the benefit of the filing date of copending U.S. Provisional Application Ser. No. 60/114,258 filed Dec. 30, 1998.

FIELD OF THE INVENTION

The present invention relates to the field of orthodontic expanders of the type which are placed in a patient's mouth and engage teeth on opposing sides of the palate. The expander is then forced apart by means of a double-threaded shaft called a retention or expansion screw to exert a lateral force on the palate to expand it. In particular, the present invention is directed to an improved hand-held and hand-activated device for torquing the expansion screw of an orthodontic expander appliance.

BACKGROUND OF THE INVENTION

There are various held-held and manually operated devices for adjusting an orthodontic expander by turning or torquing the double-threaded expansion screw. All of these devices suffer from one or more disadvantages.

One disadvantage of some prior art devices results from the fact that the torquing device itself is small enough to fit entirely within the patient's mouth. This has a primary disadvantage of blocking off the dentist's view because the hand holding and operating the torquing device covers the patient's mouth, making it difficult to insert the device in the expansion screw. Secondly, the torquing device is so small that if the dentist inadvertently drops the device while it is in a patient's mouth, it could possibly be swallowed or cause discomfort to the patient since the patient is normally positioned with his or her mouth opening upwardly. Thus, the torquing device is typically placed on a tether for safety and comfort, making manipulation of the device even more cumbersome.

Many prior art devices which are capable of torquing an expansion screw are easily dislodged from the screw, either because it is difficult accurately to use the device through a full 90° rotation of the screw as is required, or, as is equally common, while effecting a full quarter turn rotation of the expansion screw, the activating tip may slide out of the aperture in the center of the expansion screw in which the tip is received. In the case of an adjusting device becoming dislodged from the expansion screw while the dentist is turning the device, the pointed tip of the activating device has the potential to poke or scratch the tissue of the patient's mouth, causing discomfort or pain. Dentists, as well as patients, of course, are desirous of eliminating such discomfort.

Another disadvantage of some prior art devices is that they are difficult to operate in the sense that because of the structure of the device, the dentist's hand holding the device partially or substantially occludes the opening of the mouth. This restricts the amount of light that might enter the patient's mouth to illuminate the expander and adjusting mechanism, thereby rendering it more difficult to make an adjustment. Manipulating the small tool with the hand also restricts the field of vision of the dentist inside the patient's mouth.

These disadvantages are overcome by the improved device of the present invention.

SUMMARY OF THE INVENTION

The present invention provides a dental instrument capable of torquing the double-threaded expansion screw of a conventional orthodontic expander appliance with an integral device having an elongated handle and an angled activator tip. The activator tip is in the form of a wire-like extension, and it defines an angle with the axis of the handle which is either approximately 90° or slightly greater.

The length of the handle is such that the dentist may comfortably grasp the handle with his or her hand completely outside of the mouth and to the side of the mouth so that the dentist's view is not occluded. That is, the length of the handle and the angle at which the tip is directed relative to the axis or extension of the handle, are such that the hand of the dentist holding the instrument is to the side of the patient's mouth while adjusting the expander; and the dentist's hand is completely to the side of the medial plane of the patient's mouth. As used herein, the "medial plane" is a plane passing through the center of the patient's mouth and bisecting the patient's palate. Thus, when the patient is standing upright or looking in a vertical direction, the medial plane is also vertical, as is the case, normally, when a dentist is adjusting an orthodontic expander appliance.

Due to the construction of the inventive instrument, the activating tip is easily inserted in the torquing apertures of the expansion screw, the view of the user is largely unobstructed, and the user may exert more force to torque the screw than with prior devices without fear of dislodging the torquing device from the expansion screw.

Other features and advantages of the present invention include the fact that the instrument is constructed similar to a typical dental instrument having an extended handle of the type commonly employed by dentists and orthodontists for other appliances so it is more familiar to most dentists. Moreover, the new instrument can be made of more permanent metal which enables the dentist to sterilize and re-use the instrument, or it can be made of plastic as a disposable instrument, so that it can be used by the patient or associate of the patient having knowledge of what is required to be done, and then the instrument may be disposed of after use. Of primary benefit is the ease with which the user of the instrument, whether dentist or layman, can position the tip into the center torquing hole of the expansion screw of an expander appliance without obstructing his or her vision of the appliance. This greatly reduces the tendency to miss the hole in the expansion screw and perhaps poke the palate tissue of the patient. Moreover, once the instrument is properly seated in the expansion screw, the dentist or other user may place his or her index finger onto the shaft of the instrument, adjacent the handle, and thereby apply greater leverage in rotating the expansion screw to expand the appliance while maintaining a firm grip on the instrument and assuring that the instrument remains properly seated in the expansion screw during an adjustment procedure.

Other features and advantages of the present invention will be apparent to persons skilled in the art from the following detailed description of a preferred embodiment accompanied by the attached drawing wherein identical reference numerals will refer to like parts in the various views.

DETAILED DESCRIPTION OF A PREFERRED EMBODIMENT

Figure 1:
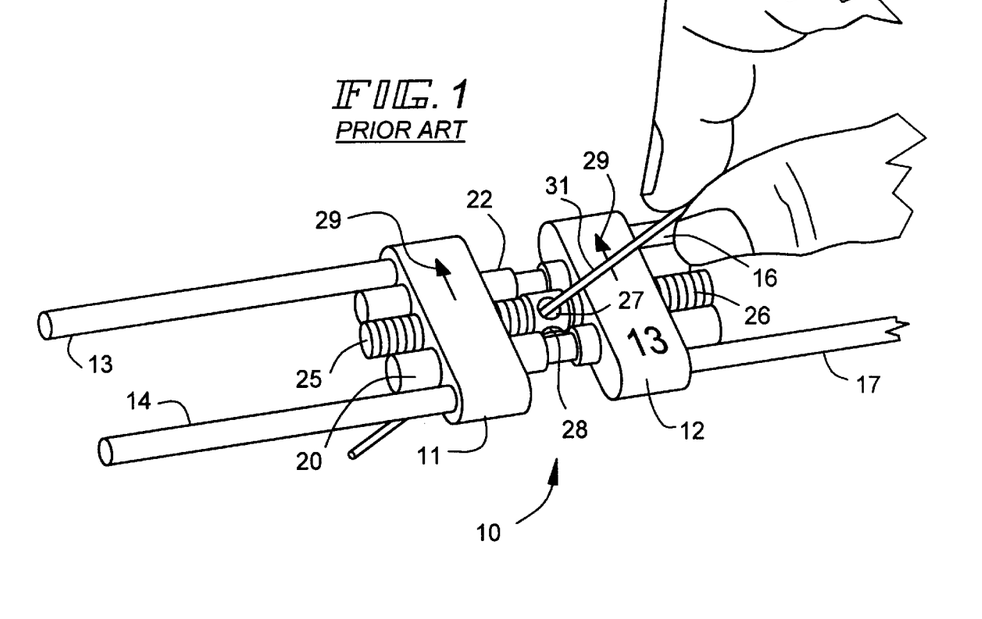
FIG. 1 is a close-up, perspective, partial view of a conventional prior art orthodontic expander being manually adjusted and tested prior to insertion into the mouth of a patient.

Referring first to FIG. 1, there is shown a known expander appliance generally designated 10 and marketed under the trademark "LEONE" by American Tooth Industries of Oxnard, Calif. The expander 10 includes first and second opposed jaws 11 and 12. A pair of wires, such as those designated 13 and 14 for the jaw 11 are rigidly secured to each jaw and extend laterally for holding and connecting to the band portions of the expander appliance. The bands surround and seat on associated teeth. Typically, there are four such bands, two on either side of the patient's mouth.

When the jaws 11, 12 are spread apart, as will be understood by those skilled in the art, the extender wires 13, 14 are placed in compression, causing the bands of the expander which engage the teeth to spread apart laterally, thereby forcing the teeth of the patient laterally to the side and away from what is referred to herein as the medial plane. The medial plane, as used herein, is a plane which is vertical if the patient is standing upright or has his or her head rearwardly but is looking upward, and which passes through the center of the palate and, of course, between the two front teeth of the patient as they would normally be disposed.

There are two corresponding wires designated 16, 17 connected to the complementary jaw 12. The corresponding bands of the expander which engage the teeth and are secured to these wires are not seen in FIG. 1 for brevity, and because they are well known in the art.

Each of the jaws 11, 12 is provided with a pair of bores. The bores on each jaw are in register with an associated bore on the complimentary jaw. Aligned bores, one on each jaw 11, 12, receive a guide pin, such as the one designated 20 seen in the lower portion of FIG. 1, and the one designated 22 in the upper portion of FIG. 1. The guide pins 20, 22 maintain alignment of the jaws of the appliance and permit the jaws to slide laterally toward and away from each other, but not to twist or turn relative to each other.

Further, each of the jaws 11, 12 includes a center, internally threaded bore for receiving respectively the opposing ends of a doubly threaded expansion screw 24. The expansion screw 24 has first and second threaded portions 25, 26 spaced by an unthreaded center portion which has two intersecting bores 27, 28 formed at right angles to one another and extending diametrically through the center of the expansion screw 24. This provides four torquing apertures in quadrature (i.e., ninety degrees apart), for receiving the activator tip of an adjustment instrument.

One of the cross bores can be seen at 27, and the other can be seen at 28 in FIG. 1. The threads 25, 26 are formed as reverse threads—that is, one is a right-hand thread and the other is a left-hand thread so that as the screw is turned in one direction, the jaws 11, 12 are forced apart, and as the expansion screw 24 is turned in the other direction, the jaws 11, 12 are pulled together.

The device as seen in FIG. 1 is in a position where an orthodontist, or dentist or other user (herein sometimes referred to as the user) has assembled the device and is torquing the expansion screw 24 to make sure that it works. In use, when the expansion screw 24 is turned in the direction of the arrows 29 on the jaws, the jaws 11, 12 expand. When the appliance is installed in the mouth of the patient the appliance is turned around (that is, the right side of the appliance in FIG. 1 is on the patient's right side), the expansion screw is expanded by a motion in which one of the cross bores in the expansion screw is moved from a forward position to a rear position, in the direction of the arrows 29. In normal operation, this is downward and toward the rear of the mouth, as mentioned, (i.e., in a counterclockwise direction when viewed from the right side of the patient). These directions and orientations are by convention, and could be reversed with the same results.

In FIG. 1, a straight pin or wire 31 may be used as an adjustment tool to make sure that the threads are operating freely and to preset the expander appliance for placement in the patient's mouth. However, it will be appreciated from FIG. 1 that the adjusting pin 31 extends well through the expander screw and thus could engage and penetrate tissue on the patient's palate if it were used when the appliance is installed in a patient's mouth.

Figure 2:
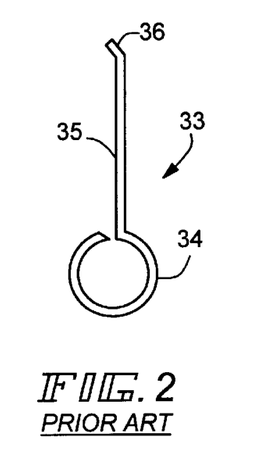
FIG. 2 is an elevation view of an expander key known in the prior art for expanding the prior art appliance of FIG. 1 after it is inserted in the mouth of a patient.

Thus, in actual usage, after the expander appliance has been installed in the patient's mouth, an adjusting key such as the one shown in FIG. 2 and designated 33 may be used. It includes a ring-shaped handle 34, a short, straight extension or shaft 35 and an inclined tip 36. The bend between the tip 36 and the extension 35 precludes extending the tip completely through the bore in the expansion screw, which might scratch the patient's mouth. On the other hand, the disadvantage is that the size of the adjusting key 33, as determined primarily by the length of the shaft 35 is such that it fits almost entirely within the patient's mouth. The shaft 35 is also placed in the medial plane to adjust the expander, so that the user's fingers are normally located partially in the patient's mouth during adjustment.

Figure 3:
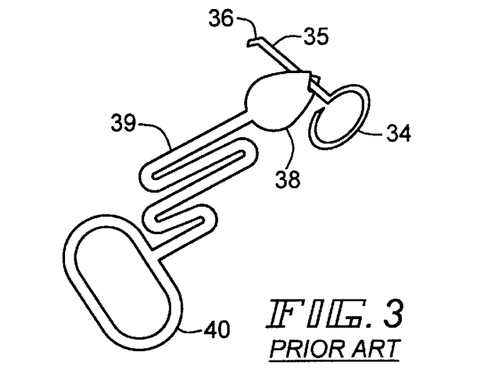
FIG. 3 is a view of the expander key of FIG. 2 with a tether and finger loop.
Figure 4:
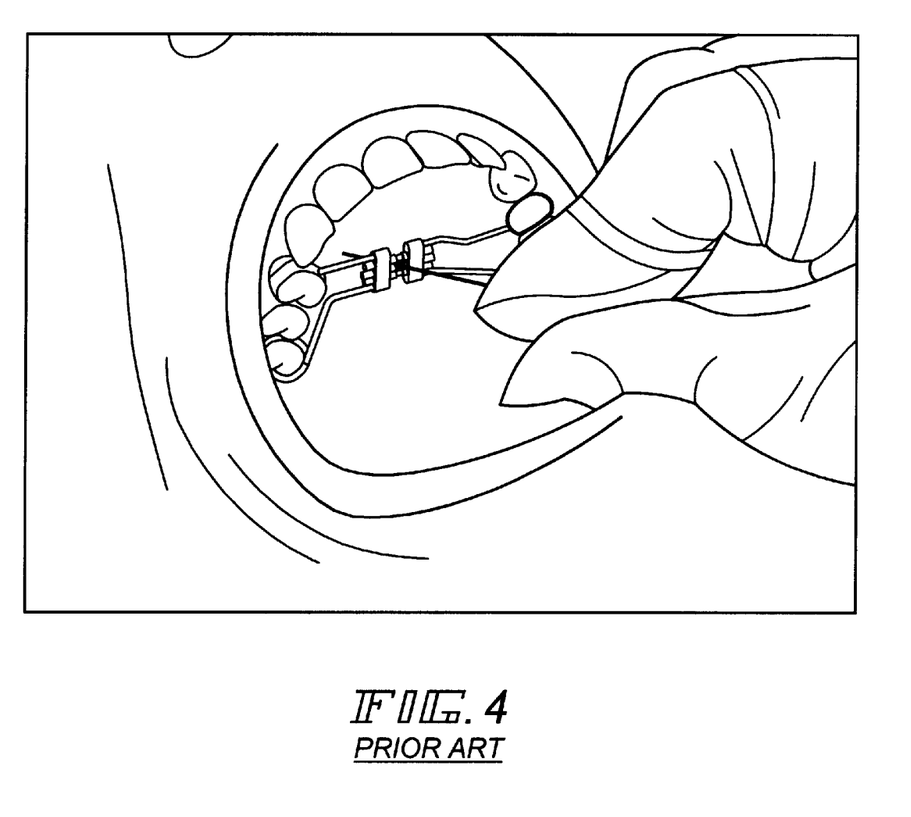
FIG. 4 is a perspective view of the prior art expander appliance of FIG. 1 being adjusted with the adjusting key of FIG. 3.

Thus, because of its small size, the key of FIG. 2 is normally provided with a tether as shown in FIG. 3. That is, the shaft 35 is embedded in a plastic molded pad 38, with the shaft 35 and adjusting tip 36 extending out one end, and with a tether 39 connected to the other end. The other end of the tether 39 is attached to an oblong ring 40 which is secured around the user's index finger, as seen in FIG. 4 which illustrates how a prior art torquing key normally is used.

Figures 5, 6:
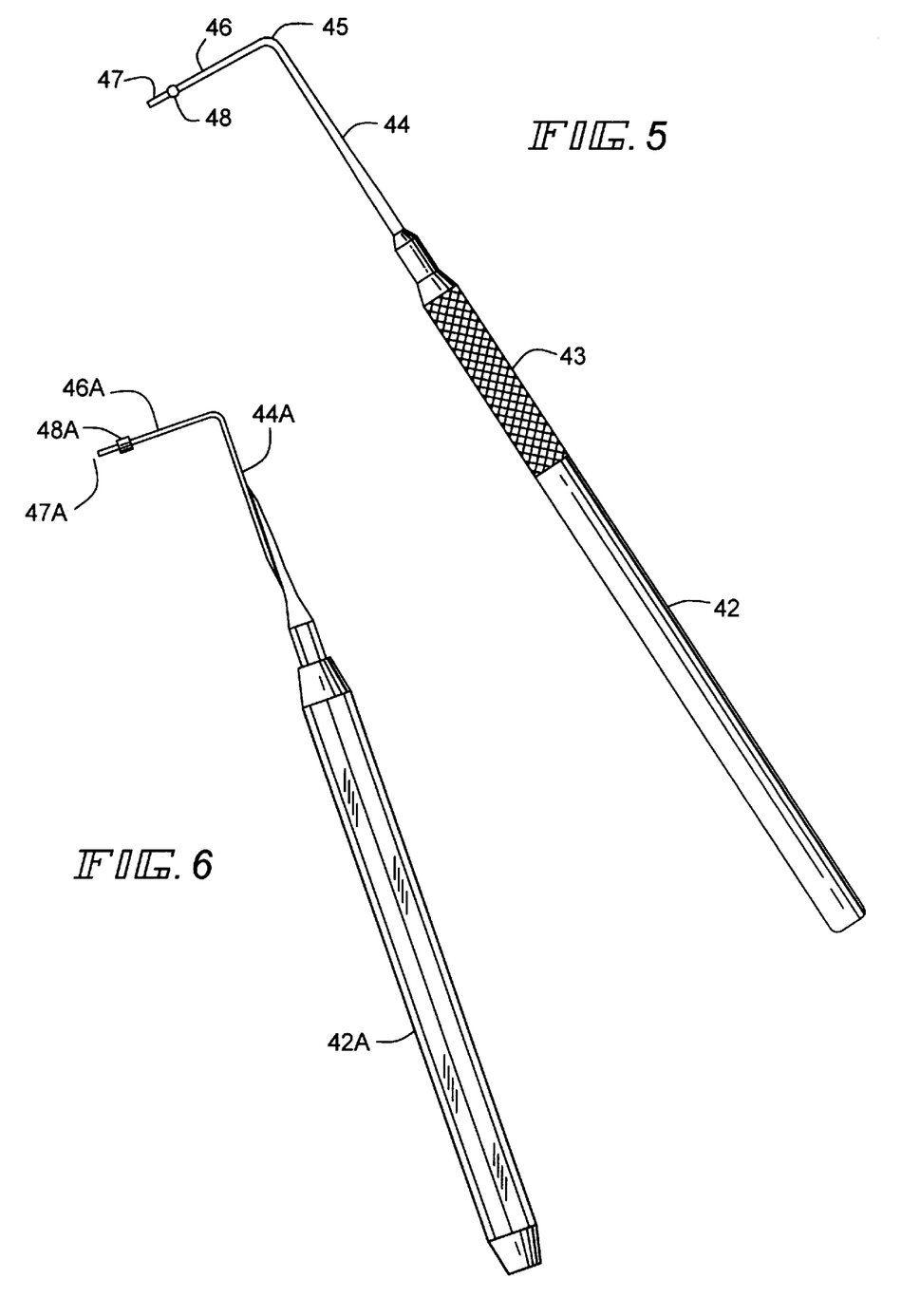
FIG. 5 is a side view of an improved expander adjusting instrument constructed according to the present invention.
FIG. 6 is a side view of an alternate embodiment of an improved expander adjusting instrument constructed according to the present invention.

Turning now to the instrument of the present invention, it contemplates no changes to the structure of the expander appliance, and that is considered an important feature. Turning then to FIG. 5, a first embodiment of the adjusting instrument of the present invention includes an elongated handle 42, a portion of which such as designated 43 may be knurled for better gripping with the fingers, if desired. Extending axially from the left side of the handle 42 is a small-diameter wire-like axial extension or shaft 44 which is bent or turned at 45 to form an angled distal extension 46. The end of the distal extension 46, designated 47, forms an activator tip and has a diameter permitting it to be inserted into the center bores of the expansion screw of the expander appliance. An enlarged stop member 48, in the form of a ball or sphere having a diameter larger than the diameter of a torquing bores 27, 28 is provided inwardly of the distal end of the tip 47 to limit the insertion of the tip 47 into the cross bores of the expansion screw. The stop member 48 preferably is spaced from the distal free end of the extension 44 by a distance which permits the tip 47 to extend through the expansion screw and slightly beyond the end of the expansion screw, but not far enough so that it contacts the palate of the patient.

Figure 7:
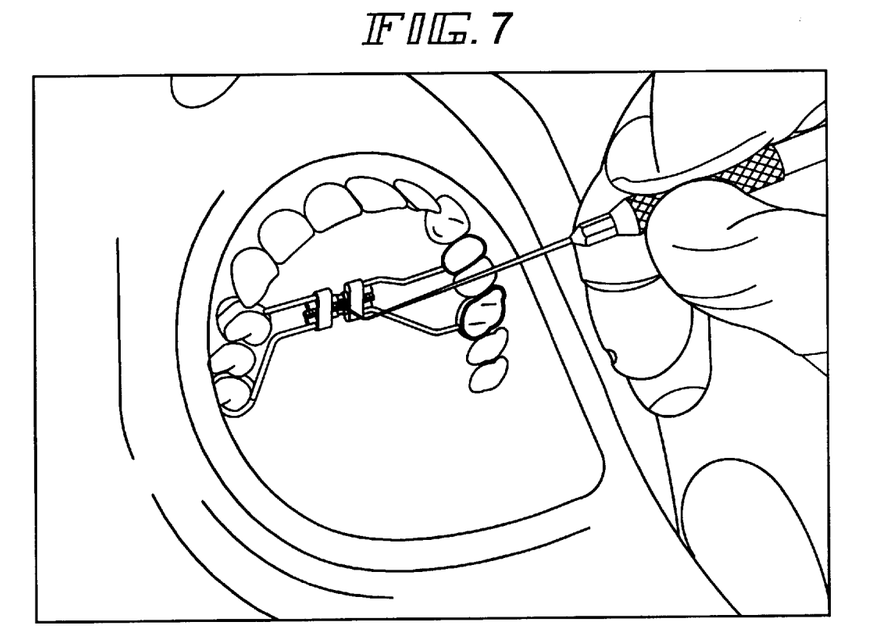
FIG. 7 is a lower frontal perspective view of the palate and upper teeth of a patient's mouth to which an expander appliance has been applied and showing how the instrument of the present invention is inserted into the expansion screw of the expander appliance without obstructing the view of the expander.
Figure 8:
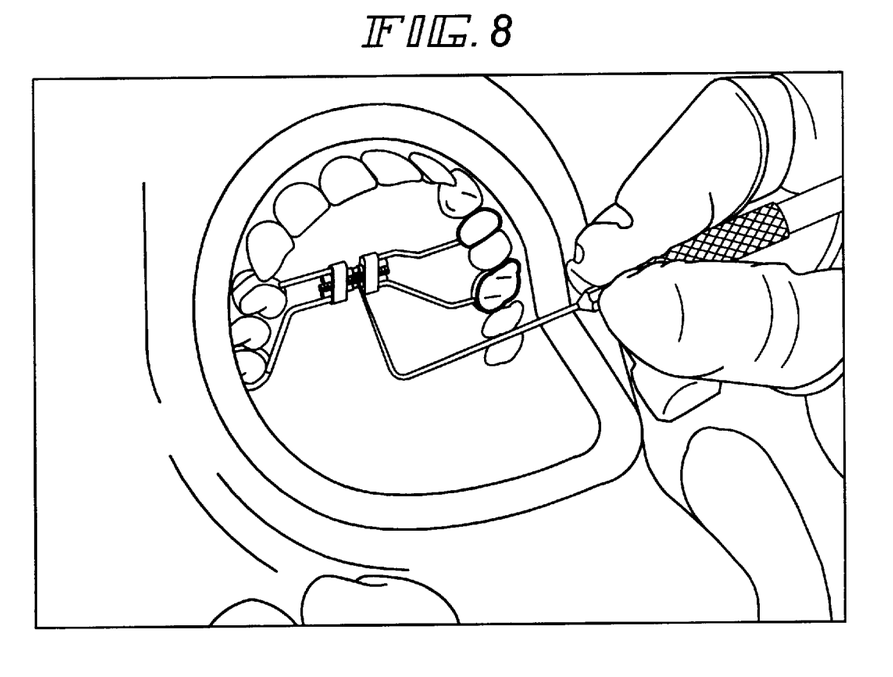
FIG. 8 is a view similar to FIG. 7 illustrating the use of the inventive instrument to turn the expansion screw a quarter turn to adjust the expander appliance laterally.

In the embodiment of FIG. 5, though it is not necessary to practice the invention, the angle which the distal extension 46 forms relative to the extension 44 is either a 90° angle or slightly obtuse, that is 92–93°. This enables the user, as seen in FIGS. 7 and 8, to insert the instrument into the patient's mouth with the hand on the side, not in front, and align the distal extension 46 of the activating portion of the instrument along the medial plane while comfortably resting the hand not only outside the patient's mouth, but well to the side, as provided by the length of the axial extension portion 44 relative to the angled distal extension 46. The length of the angled distal extension 46 is also important in that it has to be of sufficient length to permit the activating tip 47 to be firmly seated in one of the torquing bores of the expansion screw, but short enough so that the user may place his or her hand adjacent the side of the patient's face in use.

As best seen by comparing FIGS. 7 and 8, then, once the instrument is properly inserted in a torquing bore of the expansion screw, the user's hand turns the device as seen in FIG. 8, turning the expansion screw a quarter turn, in a downward and rearward motion, and bringing the aperture of the other cross torquing bore toward the front where it is then accessible in a repetitive step of the first procedure described above.

Turning now to FIG. 6, there is shown a second embodiment of the inventive instrument. Again, it has an elongated handle 42A, but the handle 42A of the instrument of FIG. 6 may have a cross section in the form of a hexagon, pentagon or any other multi-faceted shape permitting the user to obtain a better more comfortable grip. In the device of FIG. 6, the handle is provided with an axial extension 44A bent to form an angled distal extension 46A formed approximately at right angles relative to the axis of the handle 42A. The angled extension 46A also defines an activating tip 47A, which is defined by a stop 48A, in the form of a cylinder or disc. In this case the angled extension 46A is at a right angle relative to the axial extension 44A.

Figure 9:
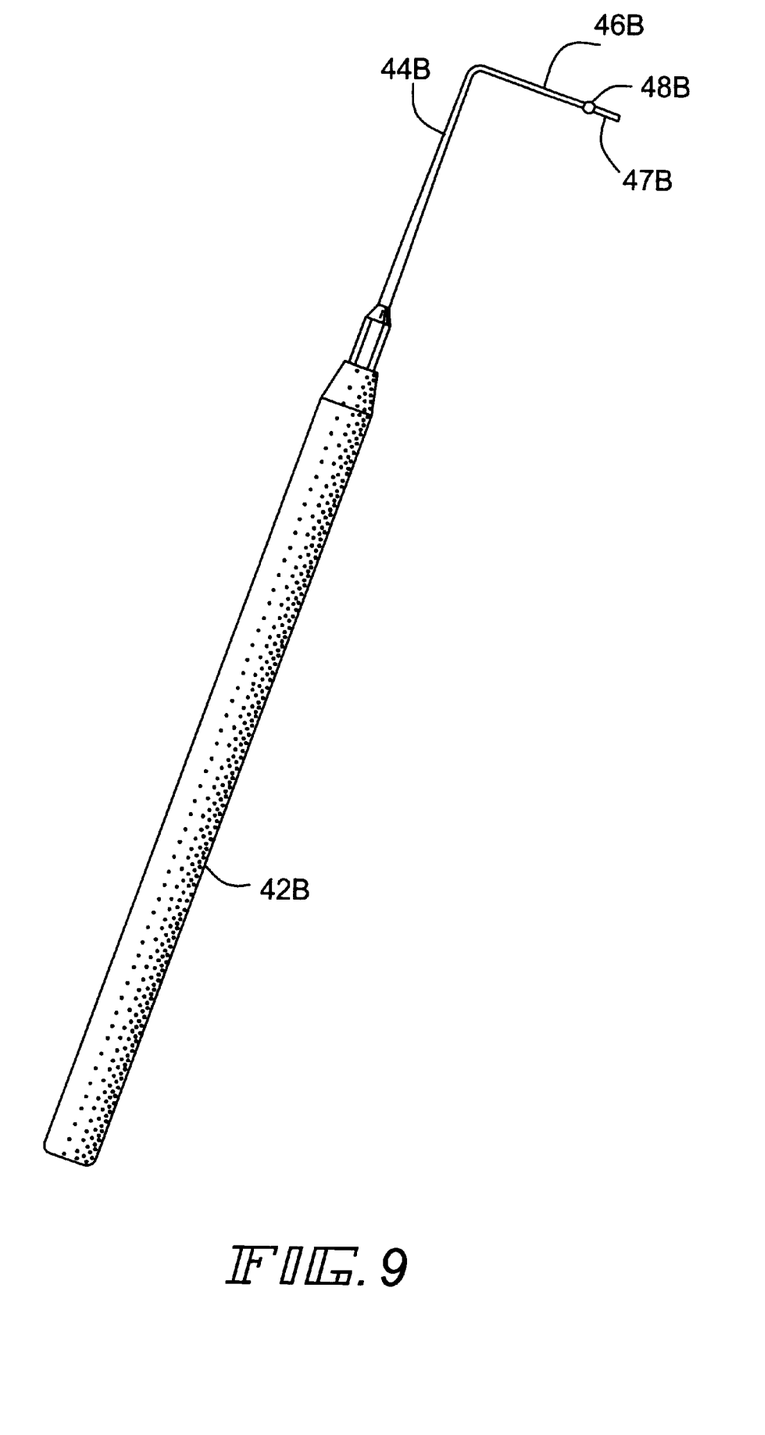
FIG. 9 is a side view of a third embodiment of the inventive adjusting instrument.

Turning now to FIG. 9, there is shown a third embodiment of the inventive instrument. It includes a handle 42B of generally cylindrical shape. An extension 44B extends axially of the handle 42B and is tapered slightly, and then bent to form an angled distal extension 46B at right angles to the extension 44B and the axis of the handle. The angled extension 46B also defines an activating tip 47B, which is defined by a stop 48B in the form of a sphere.

The shapes of the handles and the shape of the stops 48, 48A, 48B are not important aspects of the present invention. Further, the materials used in the handle and in the activating extensions are also not critical. Some users may prefer stainless steel instruments if they intend to re-use the instruments after sterilizing them. Others, particularly where the instruments may be used by the users themselves or in other settings where sterilization is not available, may be made of plastic or less expensive metal so that they may be disposed after use. In all these embodiments, the length of the handle is sufficient to be held comfortably in one hand.

Having disclosed the instrument of the present invention, it will be apparent to persons skilled in the art that the instrument of the present invention permits the user to insert the activating tip in one of the torquing bores of the expansion screw of an orthodontic expander appliance with a clear view of the patient's mouth and particularly of the remote central portion of the expander appliance. Yet, the angled distal extension 46, 46A, 46B of the instrument lies generally in the medial plane of the patient's mouth during use so that its insertion into the torquing bore is clearly visible yet readily effected. The user has accurate and immediate control of the instrument because the user's hand is immediately adjacent the patient's mouth and completely to one side of the medial plane of the patient's mouth. Further, the user may exert substantial leverage, if necessary, in torquing the expansion screw of the expander because of the length of the angled distal extension, and can apply that leverage remotely, either by twisting the handle with the hand or, if additional torque is required, as is sometimes the case, by applying a finger to the axial portion 44, 44A, 44B of the axial extension and turning the angled distal extension 46, 46A, 46B in a counterclockwise direction (when viewed from the patient's right side).

While particular embodiments of the present invention have been shown and described, it will be apparent to those skilled in the art that changes and modifications may be made without departing from the invention in its broader aspects. The matter set forth in the foregoing description and accompanying drawings is offered by way of illustration only and not as a limitation.

What is claimed is:

1. For use in combination, with an orthodontic expander appliance having an expansion screw adapted to expand the width of said expander appliance when rotated and including at least one torquing bore extending diametrically through said expansion screw, a tool comprising:

an elongated handle having an axial length permitting a user to grip with a hand;

an elongated extension extending generally from said handle in the direction of elongation thereof;

an activator tip extending from said extension at about 90° relative to the direction of elongation of said extension; and a stop member on said activator tip spaced inwardly of the distal end thereof a distance to permit insertion of the distal end into said bore of said expansion screw while said stop member limits the insertion of said activator tip into said bore, whereby the tip of said distal portion is prevented from engaging the mouth of a patient and said tool may be placed for insertion of said distal portion into said bore by hand manipulation of said handle to the side of a patient's mouth, and torquing of said bore is accomplished from the side of a patient's mouth, leaving an unobstructed view of said expansion screw.

2. The device of claim 1 wherein said handle is made of metal and includes a gnarled portion for improved gripping adjacent said extension.

3. The device of claim 2 wherein said handle has a base portion which is polygonal in cross section, providing elongated flat sides for handling.

4. The device of claim 3 wherein said extension is in the form of a wire extending axially of said handle and is bent to form said activator tip, said stop member being generally spherical.

5. The device of claim 1 wherein said handle is elongated and has a substantially circular cross section.

6. The device of claim 5 wherein said extension extends axially of one end of said handle and is tapered, said actuator tip being in the form of a wire.

7. The device of claim 6 wherein said stop member is integrally formed on said activator tip and is in the general form of a cylinder.

8. The device of claim 7 characterized in that the portion of said activator tip between said stop member and the distal end thereof is of a length not substantially greater than the diameter of said expansion screw, thereby to limit the portion of the distal end of said activator tip which is capable of extending beyond the purpose of said expansion screw to eliminate contact between said activator tip and the mouth of a patient.

9. The device of claim 1 wherein said tool is made of plastic and is disposable.

10. The device of claim 1 wherein said angle between said extension and said activator tip is in the range of 90°–93°.

11. A method of adjusting an orthodontic expander having an expansion screw comprising:

holding an instrument in one hand by grasping an elongated handle of the instrument having a distal extension bent to form an activator tip with a stop member;

placing the hand holding said instrument entirely to one side of the medial plane of the patient's mouth while inserting a distal extension of said instrument into a torquing bore of said expansion screw until a stop member on said distal extension engages said expansion screw and limits further insertion thereof; and rotating the handle of said instrument about its axis to turn said expansion screw.

12. The method of claim 10 wherein said step of rotating includes placing the index finger on an axial extension of said handle adjacent the bend therein to exert a torquing force on said expansion screw.

* * * * *

UNITED STATES PATENT AND TRADEMARK OFFICE
CERTIFICATE OF CORRECTION

PATENT NO. : 6,174,162
DATED : January 16, 20001
INVENTOR(S) : Bruno Pozzi

It is certified that error appears in the above-indentified patent and that said Letters Patent is hereby corrected as shown below:

Column 8: Line 18, delete "10" and insert -- 11 --.

Signed and Sealed this

Eighth Day of May, 2001

Attest:

NICHOLAS P. GODICI

Attesting Officer

Acting Director of the United States Patent and Trademark Office